US012721730B2

(12) United States Patent
Picard et al.

(10) Patent No.: US 12,721,730 B2
(45) Date of Patent: Sep. 1, 2026

(54) METHOD FOR DESIGNING A JOINT PROSTHESIS

(71) Applicant: Prometheus Regeneration R&D Limited, Glasgow (GB)

(72) Inventors: Frederic Picard, Newton Mearns (GB); Guillaume Picard, Newton Mearns (GB); Angela H. Deakin, Cumbernauld (GB)

(73) Assignee: Prometheus Regeneration R&D Limited, Glasgow (GB)

( * ) Notice: Subject to any disclaimer, the term of this patent is extended or adjusted under 35 U.S.C. 154(b) by 873 days.

(21) Appl. No.: 17/624,624

(22) PCT Filed: Jul. 2, 2020

(86) PCT No.: PCT/EP2020/068748

§ 371 (c)(1),
(2) Date: Jan. 4, 2022

(87) PCT Pub. No.: WO2021/008892

PCT Pub. Date: Jan. 21, 2021

(65) Prior Publication Data

US 2022/0257384 A1 Aug. 18, 2022

(30) Foreign Application Priority Data

Jul. 17, 2019 (GB) ..................................... 1910248

(51) Int. Cl.
*A61F 2/30* (2006.01)
*A61F 2/38* (2006.01)
(Continued)

(52) U.S. Cl.
CPC ............ *A61F 2/30942* (2013.01); *A61F 2/38* (2013.01); *A61F 2/4684* (2013.01);
(Continued)

(58) Field of Classification Search
CPC ............................... A61F 2/389; A61F 2/3859
See application file for complete search history.

(56) References Cited

U.S. PATENT DOCUMENTS 4,841,975 A * 6/1989 Woolson .............. A61B 17/154 600/587
5,520,694 A * 5/1996 Dance .................. A61B 17/154 606/88

(Continued)

FOREIGN PATENT DOCUMENTS

EP 3266419 A1 1/2018
WO 2012112694 A2 8/2012

(Continued)

OTHER PUBLICATIONS

Alho et al. "Assessment of anteroposterior [AP] knee joint laxity using non-invasive navigation in healthy volunteers" The Bone & Joint Journal, 98-B(Supp 5):20 (2016).

(Continued)

*Primary Examiner* — Jacqueline Woznicki
(74) *Attorney, Agent, or Firm* — Myers Bigel, P.A.

(57) ABSTRACT

A method for designing a two-part joint prosthesis (830) comprises: providing kinematic data of a subject's joint under load; and designing the joint prosthesis using the kinematic data, wherein the working surfaces of the two-part prosthesis comprise, consist essentially of or consist of cellular material. Advantageously, the method may not require any intra-operative adjustments to replace one or more of the components (831, 832), e.g. with a component of a different size. In particular, if components are made of biological tissues, such as a patient's own cells, it is advantageous to design and produce an implant that requires no adjustments intra-operatively as each implant may be manufactured specifically for each patient, and the time and costs
(Continued)

of producing a range of sizes, most of which would not be required, would otherwise be prohibitive.

18 Claims, 13 Drawing Sheets

(51) Int. Cl.

| | |
|---|---|
| ***A61F 2/46*** | (2006.01) |
| ***B29C 64/386*** | (2017.01) |
| ***B33Y 50/00*** | (2015.01) |
| ***B33Y 80/00*** | (2015.01) |
| ***G16H 50/50*** | (2018.01) |
| *B29L 31/00* | (2006.01) |

(52) U.S. Cl.
CPC ............ *B29C 64/386* (2017.08); *B33Y 50/00* (2014.12); *B33Y 80/00* (2014.12); *G16H 50/50* (2018.01); *A61F 2/3094* (2013.01); *A61F 2002/30952* (2013.01); *A61F 2002/30985* (2013.01); *A61F 2002/4666* (2013.01); *A61F 2310/00359* (2013.01); *B29L 2031/7532* (2013.01)

(56) References Cited

U.S. PATENT DOCUMENTS

| | | | | |
|---|---|---|---|---|
| 5,937,430 | A | 8/1999 | Saitoh et al. | |
| 8,062,302 | B2 * | 11/2011 | Lang | A61B 17/1739 606/87 |
| 2008/0281328 | A1 * | 11/2008 | Lang | A61F 2/30942 606/87 |
| 2008/0294258 | A1 * | 11/2008 | Revie | A61B 5/6878 623/18.11 |
| 2011/0136162 | A1 * | 6/2011 | Sun | B01L 3/502761 118/723 R |
| 2011/0305379 | A1 * | 12/2011 | Mahfouz | G06F 17/18 345/419 |
| 2013/0185310 | A1 * | 7/2013 | De Guise | G06F 16/24578 703/11 |
| 2013/0203031 | A1 | 8/2013 | McKinnon et al. | |
| 2014/0222157 | A1 * | 8/2014 | Al Hares | A61F 2/30942 703/1 |
| 2014/0228860 | A1 * | 8/2014 | Steines | A61B 34/10 606/130 |
| 2015/0057756 | A1 | 2/2015 | Lang et al. | |
| 2015/0127009 | A1 * | 5/2015 | Berend | A61F 2/4684 606/88 |
| 2015/0250552 | A1 * | 9/2015 | Radermacher | A61F 2/46 703/11 |
| 2016/0045317 | A1 * | 2/2016 | Lang | A61F 2/30942 700/98 |
| 2016/0174994 | A1 * | 6/2016 | Hafez | A61B 17/157 606/88 |
| 2016/0317309 | A1 * | 11/2016 | Al Hares | A61F 2/30942 |
| 2017/0042619 | A1 | 2/2017 | Brooks | |
| 2017/0065350 | A1 | 3/2017 | Dossett et al. | |
| 2017/0281353 | A1 * | 10/2017 | Al Hares | A61F 2/38 |
| 2018/0021138 | A1 * | 1/2018 | Estes | A61F 2/30756 623/16.11 |
| 2018/0028325 | A1 * | 2/2018 | Bojarski | A61F 2/3859 |
| 2018/0235641 | A1 * | 8/2018 | McAuliffe | A61B 17/155 |
| 2018/0289286 | A1 | 10/2018 | Agarwal et al. | |
| 2018/0360544 | A1 | 12/2018 | Vanheule et al. | |
| 2019/0008532 | A1 * | 1/2019 | Fitz | G06F 30/00 |
| 2020/0138518 | A1 * | 5/2020 | Lang | A61B 17/1666 |
| 2022/0079678 | A1 * | 3/2022 | McKinnon | G16H 30/40 |
| 2022/0257384 | A1 * | 8/2022 | Picard | G16H 50/50 |
| 2022/0273281 | A1 * | 9/2022 | Mckinnon | A61B 17/025 |
| 2023/0233229 | A1 * | 7/2023 | Picard | A61B 17/3468 606/53 |
| 2023/0377714 | A1 * | 11/2023 | Liarno | G16H 20/40 |

FOREIGN PATENT DOCUMENTS

| | | | | |
|---|---|---|---|---|
| WO | 2013131066 | A1 | 9/2013 | |
| WO | 2014145267 | A1 | 9/2014 | |
| WO | 2017196817 | A1 | 11/2017 | |
| WO | 2017214656 | A1 | 12/2017 | |
| WO | 2017214736 | A1 | 12/2017 | |
| WO | 2017214836 | A1 | 12/2017 | |
| WO | 2018067966 | A1 | 4/2018 | |
| WO | WO-2024243383 | A1 * | 11/2024 | A61B 34/30 |

OTHER PUBLICATIONS

Brown et al. "Lower limb alignment becomes more varus and hyperextended from supine to bipedal stance in asymptomatic, osteoarthritic and prosthetic neutral or varus knees" Knee Surgery, Sports Traumatology, Arthroscopy, 27(5):1635-1641 (2019).

Clarke et al. "Non-invasive computer-assisted measurement of knee alignment" Computer Aided Surgery, 17:29-39 (2012).

Clarke et al. "Standardising the clinical assessment of coronal knee laxity" Journal of Engineering in Medicine, 226 (9):699-708 (2012).

Henderson et al. "Assessment of knee alignment with varus and valgus force through the range of flexion with non-invasive navigation" Journal of Medical Engineering & Technology, 41(6):444-459 (2017).

Heyse et al. "UKA in combination with PFR at average 12-year follow-up" Archives of Orthopaedic and Trauma Surgery, 130(10):1227-1230 (2010).

Kurosawa et al. "Geometry and motion of the knee for implant and orthotic design" Journal of Biomechanics, 18 (7):487-499 (1985).

Russell et al. "Non-invasive quantification of lower limb mechanical alignment in flexion" Computer Aided Surgery, 19(406):64-70 (2014).

Russell et al. "Non-invasive, non-radiological quantification of anteroposterior knee joint ligamentous laxity" Bone and Joint Research, 2(11):233-237 (2013).

Russell et al. "Quantitative measurement lower limb mechanical alignment and coronal knee laxity in early flexion" The Knee, 21(6):1063-1068 (2014).

Russell et al. Repeatability and accuracy of a non-invasive method of measuring internal and external rotation of the tibia. Knee Surgery, Sports Traumatology, Arthroscopy, 22(8):1771-1777 (2014).

International Search Report and the Written Opinion of the International Searching Authority corresponding to International Patent Application No. PCT/EP2020/068748 (12 pages) (mailed Oct. 5, 2020).

* cited by examiner

METHOD FOR DESIGNING A JOINT PROSTHESIS

TECHNICAL FIELD

Embodiments of the invention relate to a method for designing a joint prosthesis, and to a joint prosthesis designed and/or made according to such method.

BACKGROUND

The human body contains several types of joints, which provide articulated connections between bones in the body, and are configured to allow various degrees of movement. The knee is a joint which provides, in particular, an articulated connection between the femur and the tibia and a connection between the femur and the patella. In the knee joint, the femur and the tibia have complementary shapes which allows the femur and the tibia to move in relation to each other with a partially constrained path. The bone surfaces at the joint are protected by cartilage which provides a lubricated contact surface and ensures that the joint surfaces can slide easily over each other.

The knee is particularly prone to injury and also to damage as a result of a number of conditions, such as osteoarthritis. When the knee is damaged to the extent that the function of the knee is compromised and/or that the pain suffered by a subject is too great, a surgical procedure known as knee replacement is often considered. Knee replacement can involve partial knee replacement (known as unicompartmental knee arthroplasty—UKA or patello-femoral joint replacement—PFJR) or total knee replacement (known as total knee arthroplasty—TKA). UKA involves replacing the femoral, tibial and/or patellar surfaces only in the compartment of the knee which is damaged (medial femorotibial or lateral femorotibial compartments or patellofemoral compartment), whereas TKA involves replacing the whole knee joint on both the femoral and the tibial side of the knee as well as the patellofemoral joint in some cases.

Conventional knee replacement implants consist of three parts:

- a femoral component usually made of metal or rarely of ceramic;
- a tibial component made of metal (so-called metal-back) or a synthetic polymer material (typically polyethylene (PE)) or rarely of ceramic; and
- an insert made of a synthetic polymer material (typically polyethylene (PE)), configured to provide a contact surface between the femoral component and the tibial component. The insert is generally attached to the tibial side (metal-back or ceramic base), and provides a contact surface to cooperate with and act against the femoral component.
- in some cases the tibial component and insert are made as one piece of polyethylene (known as an "all poly" tibia) thus generating a two-component implant that mimics a three-component implant.

These parts are typically available in a range of predetermined sizes.

Prior to carrying out a knee replacement operation the surgeon will typically use some type of medical imaging (X-ray, CT, MRI, etc) and software to assess the patient's knee and select the size or sizes of each component that are considered to fit best the bone anatomy of the patient.

During the operation the surgeon will make cuts to parts of the femur and tibia and sometimes the patella in order to fit these components of pre-selected sizes and to correct any malalignment of the lower limb or in the joint itself. Unfortunately, this "templating" procedure cannot account for any variation in the soft tissues of the knee (such as surrounding tendons and ligaments) as the stiffness/tightness (or laxity) of these tissues cannot be assessed using static medical images. Such variations can cause the corrected knee to be too "tight" or too "loose". If this is the case, then the knee needs to "balanced". With the conventional three-component design this is typically addressed by adjusting the dimensions of the polyethylene insert: if the knee is too tight then a thinner insert may be used, and if the knee is too loose then a thicker insert may be used. If an all poly tibia is being used, different thickness of component can be trialled in the same way as changing the insert thickness. This allows the surgeon to correct any malalignment and to accurately balance the knee during the operation.

A problem with this conventional approach is the need for intra-operative adjustment of one or more components of the knee prosthesis to achieve a satisfactory outcome. This is a particular issue if components of different sizes are not available intra-operatively.

A number of prior art publications have attempted to improve the design of knee replacement prostheses and/or associated surgical procedures, including US2014222157A (A L HARES et al), US2015250552A (RADERMACHER et al), WO17196817A1 (VARADARAJAN et al), US2013203031A (MCKINNON et al), US2016045317A (LANG et al), WO12112694A2 (BOJARSKI et al), EP3266419A1 (EP3266419A1 et al), US2015057756A (LANG et al), US2014228860A1 (STEINES et al) and US2017042619A1 (BROOKS). However, the methods disclosed in these documents still rely on the use of a three-part knee implant and/or on the intra-operative adjustment of one or more components of the implant.

It is an object of the present invention to mitigate or alleviate one or more of the disadvantages associated with the prior art.

SUMMARY

According to a first aspect of the invention, there is provided a method for designing a two-part joint prosthesis, the method comprising:

providing kinematic data of a subject's joint under load; and designing the joint prosthesis using the kinematic data.

The method may comprise constructing the two-part joint prosthesis.

Advantageously, the method may not require any intra-operative adjustments to replace one or more of the components, e.g. with a component of a different size. In particular, if components are made of biological tissues, such as a patient's own cells, it is advantageous to design and produce an implant that requires no adjustments intra-operatively as each implant may be manufactured specifically for each patient, and the time and costs of producing a range of sizes, most of which would not be required, would otherwise be prohibitive.

Preferably, the joint may be a knee.

The joint prosthesis may be a knee prosthesis.

The knee prosthesis may comprise a femoral component and a tibial component, or a femoral component and a patellar component. The method may comprise constructing one or both of the femoral component and the tibial component, or the femoral and the patella component.

The knee prosthesis may comprise a femoral component, a tibial component, and a patellar component. The method may comprise constructing one or more of the femoral component, the tibial component, and the patellar component It will be understood that, depending on the condition of the subject's knee, it may be necessary to replace either one, or both, of the medial compartment and of the lateral compartment and/or the patellofemoral component. For example, if only one of the compartments may need to be replaced a partial knee replacement (UKA) is required. Thus, the method may comprise constructing a femoral component or a tibial component or both for one or other of the compartments of the knee. In the case that only one component is required, the other of the femoral or tibial component may comprise or may be defined by the natural femur or tibia of the subject.

If a total knee replacement (TKA) is required, the method may comprise constructing both a femoral component and a tibial component which replace the entire surface of the femur and tibia respectively, and in some cases also the patella at the same time.

The prosthesis, may be devoid of and/or may not comprise or may not be provided with an insert. By such provision, the prosthesis may be defined as a two-part prosthesis. The designing of a two-part prosthesis which is free of an insert (typically a PE insert) between the femoral component and the tibial component and which does not require intra-operative adjustment through using components of different sizes, may be particularly advantageous in the context of a bioprinted prosthesis. With a 3D bioprinted prosthesis, in which the prosthesis is generated from cells, which may be allograft or autograft cells, the working surfaces of the prosthesis, e.g. of the knee prosthesis, are not made of synthetic materials such as metal or polymers, but comprise, consist essentially of or consist of cellular material. Thus, the implant or prosthesis may be designed to replicate the normal anatomy of the subject with two complementary components. Typically, the surfaces of such bioprinted femoral, tibial and/or patellar components may comprise, may consist essentially of or may consist of hyaline cartilage and/or the supporting structures may comprise, may consist essentially of or may consist of subchondral bone and bone. In the case of a 3D bioprinted prosthesis a patient-specific two-component prothesis would be prepared in advance. This particular design of prosthesis i.e. two-component only, means that it is not possible to adjust the fit of the prosthesis intra-operatively for a knee that is "too tight" or "too loose" as per the current three-component design. This requires the components to be designed prior to the operation to be a precise fit to the patient and to give a "balance" knee with no adjustment. As such, the present method may allow the design and manufacture of a two-part joint prosthesis which can be made from 3D bioprinted cells and does not require the provision of a variable sized insert to enable the knee to be "balanced". Preferably, the method may take account not only of the bony anatomy of the subject, as in conventional methods, but also of soft tissues including, for example, cartilage and/or ligaments.

While conventional methods require the adjustment and/or resizing of such an insert to account for a subject's deformity, e.g. deformity in lower limb alignment, and/or for any imperfection in the fit of the prosthesis, the present inventors have discovered a solution for designing a two-part prosthesis or implant which does not require such an insert, and which may allow for correction of deformities in a subject's joint, e.g. knee without the need for any intra-operative adjustments.

The method may comprise determining the desired size of the prosthesis, e.g. of the femoral component and/or of the tibial component. The method may comprise determining one or more dimensions, e.g. the thickness of femoral component and/or of the tibial component. The method may comprise determining one or more dimensions, e.g. the thickness of, the tibial component, for example with respect to one or more of the following constraints: cartilage thickness, thickness of sub-chondral structure, and underlying bony structure (cancellous bone), knee kinematics.

The method may comprise performing medical imaging of a subject's joint, e.g. knee. The method may comprise performing medical imaging using Magnetic Resonance Imaging (MRI), X-ray, computerized tomography (CT), etc.

The method may comprise generating a three-dimensional (3D) image of the joint, e.g., knee. The method may comprise determining and/or generating mechanical axes of femur and/or tibia. The method may comprise determining and/or generating anatomical axes of femur and/or tibia. The method may comprise determining and or assessing any difference between the mechanical and anatomical axes of femur and/or of tibia. For example, the method may comprise identifying the presence or absence of, and/or may comprise measuring, a varus alignment or a valgus alignment of a subject's leg.

The method may comprise performing a preliminary implant assessment. The preliminary implant assessment may be based on a subject's bone anatomy.

The method may comprise selecting one or more components of an implant, e.g. a femoral and/or a tibial component of a knee implant, based on the three-dimensional (3D) image of the joint, e.g., knee. The method may comprise selecting one or more sizes of one or more components, e.g. from a range of pre-determined sizes, for example one or more sizes which may be considered to fit best the bone anatomy of the subject.

Existing methods and software, e.g. Materialise Mimics Care Suite (Materialise, Belgium), already allow a user to generate a 3D model of an implant for 3D printing based on a 3D medical image of a subject's anatomical part. However, this approach does not take into account any dynamic kinematic data and/or may still require the use of intra-operative adjustment of one or more components of the implant to correct any defects or deformities.

The method may comprise performing a preliminary or first adjustment of the implant design.

The method may comprise modifying the design and/or adjusting the designed implant based on one or more parameters selected from the list consisting of:

- Subject's cartilage dimensions, e.g. thickness, in the subject's joint, e.g. knee;
- cartilage damage in the subject's joint, e.g. knee;
- amount of bone resection which may depend on overall implant sizes.

This may allow the implant designed by the present method to fit a/the normal joint line of the subject.

The method may comprise selecting attachment means for implanting the prosthesis or implant, e.g. screws, pegs, or the like.

The method may comprise performing a second adjustment of the implant design.

The method may comprise determining and/or adjusting the dimensions of one or more components of the implant design. The method may comprise determining and/or adjusting the dimensions of one or more components of the implant design in a generally transverse or axial plane. The method may comprise determining and/or adjusting the dimensions of one or more components of the implant design in an antero-posterior (AP) direction and/or in a medio-lateral (ML) direction. The method may comprise determining and/or adjusting the dimensions of one or more components of the implant design in a plane about 80-100 degrees, e.g. in a plane about 85-95 degrees, e.g. in a plane about 90 degrees with respect to the tibial coronal mechanical alignment, and/or typically within 5 to 6 degrees of slope to the tibial sagittal mechanical alignment.

The method may comprise performing a third adjustment of the implant design.

The terms "first adjustment", "second adjustment" and "third adjustment" used herein will not be construed as necessarily cumulative or sequential. For example, the method may comprise performing the third adjustment, without the first and/or second adjustment.

The method may comprise determining and/or adjusting the thickness of at least one of the components of the implant design. Typically, the method may comprise determining and/or adjusting the thickness of the tibial component.

As mentioned above, typically, the thickness of the insert used in a conventional 3-part implant or the thickness of an all poly tibial component is adjusted intra-operatively to correct any defects or deformities. Alternatively, or additionally, conventional methods may comprise performing intra-operative cut adjustments to the tibial and/or femoral bone(s) to which the implant is intended to be fixed.

The method of the present invention may comprise determining and/or adjusting the dimensions, e.g. thickness, of at least one of the components of the implant design, e.g. of the tibial component, based on dynamic kinematic data of the subject's joint, e.g. knee.

The method may comprise obtaining kinematic data of a subject's joint, e.g. knee.

The method may comprise obtaining kinematic data of a subject's joint, e.g. knee, under load. When the joint is a knee, the method may comprise obtaining kinematic data of a subject's knee under load which may comprise specific externally applied loads and/or full weight-bearing (WB) conditions. Advantageously, the method may comprise obtaining kinematic data of a subject's knee under load in a longitudinal plane of the human body. The plane may be one or more planes selected from the coronal plane, the sagittal plane and the transverse plane. The method may comprise obtaining kinematic data of a subject's knee under load in the coronal plane. The coronal plane will be herein understood as the plane dividing the subject's body into an anterior or frontal side and a posterior or dorsal side.

The method may comprise using a non-invasive measuring apparatus.

The method may comprise measuring alignment of a subject's joint, e.g. knee, in the coronal plane.

The method may comprise non-invasive measurement of the alignment of a subject's joint, e.g. knee, in the coronal plane. The method may comprise using a non-invasive measurement apparatus such as PhysioPilot®. This apparatus and/or method may allow non-invasive measurement of knee kinematics. The method may allow numerical quantification of the movement of a subject's knee as an angle (°) and/or as a displacement (mm) value.

Further description of the methodology and features associated with PhysioPilot® is disclosed in [1] J V Clarke, P E Riches, F Picard, A H Deakin. Non-invasive computer-assisted measurement of knee alignment. Computer Aided Surgery 2012; 17:29-39, [2] J V Clarke, W T Wilson, S C Wearing, F Picard, P E Riches, A H Deakin. Standardising the clinical assessment of coronal knee laxity. Journal of Engineering in Medicine 2012; 226(9):699-708, [3] D Russell, A H Deakin, Q A Fogg, F Picard. Non-invasive quantification of lower limb mechanical alignment in flexion. Computer Aided Surgery 2014; 19(406):64-70, [4] D F Russell, A H Deakin, Q A Fogg, F Picard. Quantitative measurement lower limb mechanical alignment and coronal knee laxity in early flexion. The Knee 2014; 21(6):1063-1068, [5] D F Russell, A H Deakin, Q A Fogg, F Picard. Non-invasive, non-radiological quantification of anteroposterior knee joint ligamentous laxity. Bone and Joint Research 2013; 2(11):233-237, [6] D F Russell, A H Deakin, Q A Fogg, F Picard. Repeatability and accuracy of a non-invasive method of measuring internal and external rotation of the tibia. Knee Surgery, Sports Traumatology, Arthroscopy 2014; 22(8):1771-1777, [7] M J C Brown, A H Deakin, F Picard, P E Riches, J V Clarke. Lower limb alignment becomes more varus and hyperextended from supine to bipedal stance in asymptomatic, osteoarthritic and prosthetic neutral or varus knees. Knee Surg Sports Traumatol Arthrosc. 2019; 27(5):1635-1641, [8] F Henderson, R Alho, P Riches, F Picard. Assessment of knee alignment with varus and valgus force through the range of flexion with non-invasive navigation. J Med Eng Technol. 2017; 41(6):444-459, and [9] R Alho, F Henderson, P Rowe, A Deakin, J Clarke, F Picard. Assessment of anteroposterior [AP] knee joint laxity using non-invasive navigation in healthy volunteers. Bone Joint J 2016; 98-B(SUPP 5):20 which are all incorporated herein by reference.

The method may comprise measuring alignment of a subject's joint, e.g. knee, in the coronal plane, without load and with load i.e. specific externally applied load or under full weight-bearing conditions.

The method may comprise measuring alignment of a subject's joint, e.g. knee, in the coronal plane, without load at one or more degrees of flexion of the joint, e.g. knee, for example between about 0° and about 100° of knee flexion, e.g. between about 0° and about 90° of knee flexion, e.g. between about 0° and about 600 of knee flexion, e.g. between about 0° and about 45° of knee flexion.

The method may comprise measuring alignment of a subject's joint, e.g. knee, in the coronal plane, under load, e.g., full weight-bearing, at one or more degrees of flexion of the joint, e.g. knee, for example between about 0° and about 1000 of knee flexion, e.g. between about 0° and about 90° of knee flexion, e.g. between about 0° and about 60° of knee flexion, e.g. between about 0° and about 45° of knee flexion.

The method may comprise measuring alignment of a subject's joint, e.g. knee, in the coronal plane, under application of an external force on the subject's joint. Preferably, the force applied may be selected so as to reduce or correct a deformity, e.g. a varus deformity or a valgus deformity, for example to reduce or correct the deformity to a predetermined value. Preferably the force applied may be selected so as to reduce or correct a deformity e.g. a varus deformity or valgus deformity to the limiting value as limited by the existing knee soft tissue envelope. The force may be applied in the coronal plane. The method may comprise measuring alignment of a subject's joint, e.g. knee, in the coronal plane, under application of an/the external force at one or more degrees of flexion of the joint, e.g. knee, for example between about 0° and about 100° of knee flexion, e.g. between about 0° and about 90° of knee flexion, e.g. between about 0° and about 60° of knee flexion, e.g. between about 0° and about 45° of knee flexion. The method may comprise measuring both of a subject's joints e.g. both knees.

The skilled person will understand that the predetermined value associated with reduction or correction of a/the deformity may depend on the type of joint in question, the severity of the deformation, the condition of the knee, and/or the type of arthroplasty being considered (UKA or TKA). The method may comprise selecting the predetermined value. Typically, the predetermined value may be in the range of about 0-5°, e.g. about 1-4°. The skilled person will understand that the limiting value associated with reduction or correction of a/the deformity as defined by the existing soft tissue envelope may depend on the type of joint in question, the severity of the deformation, the condition of the knee, and/or the type of arthroplasty being considered (UKA or TKA). The method may comprise selecting this limiting value.

The method may comprise processing data obtained during non-invasive measurement of the alignment of a subject's joint, e.g. knee, in the coronal plane.

The method may comprise determining a degree or angle of correction, typically a desired degree of correction in the patient's knee, e.g. in the coronal plane. Typically, the alignment of a subject's joint, e.g. knee, in the coronal plane, with and/or without load, may vary depending on the degree of flexion of the joint. As such, the inventors have realised that it is not desirable to select an arbitrary level of correction, for example based on a specific or single degree of flexion.

The method may comprise calculating the difference between the alignment of the subject's joint without load and under application of an external force, which may comprise a predetermined value or values or limiting value or values, for one or more, typically for each, of the selected degrees of flexion of the joint, thus obtaining a number of values for the difference.

Calculating the values for the difference at each flexion may allow a user to apply these differences as target corrections in the pre-operatively modelling and design of the subject's knee prosthesis. The method may comprise calculating an average of the difference values. For example, the method may comprise calculating the mean or the median of the difference values.

Calculating the average, e.g. mean or median, may allow a user to apply this average difference as a target correction in the pre-operatively modelling and design of the subject's knee prosthesis.

The target correction or corrections may be used to design the two-part joint prosthesis, e.g. one or both components of the knee implant. By such provision the target correction may be implemented, in use, over the entire range of flexion of the knee which can be expected post-operatively.

The method may comprise designing the two-part joint prosthesis, e.g. to take into account the target correction.

The method may comprise using one or more femur designs. The method may comprise using a single-radius design and/or a dual-radius design and/or a complex multi-radius design. The method may comprise using two femur designs, e.g. a single-radius design and a dual-radius design.

The method may comprise creating a 3D model of the joint prosthesis.

The method may comprise manufacturing the joint prosthesis, e.g. one or both components thereof.

The method may comprise manufacturing the joint prosthesis using 3D bioprinting.

The structure of one or more parts of the product may be represented digitally in the form of a design file. A design file, or computer aided design (CAD) file, is a configuration file that encodes one or more of the surface or volumetric configuration of the shape of the product. That is, a design file represents the geometrical arrangement or shape of the product.

Design files can take any now known or later developed file format. For example, design files may be in the Stereolithography or "Standard Tessellation Language" (.stl) format which was created for stereolithography CAD programs of 3D Systems, or the Additive Manufacturing File (.amf) format, which is an American Society of Mechanical Engineers (ASME) standard that is an extensible markup-language (XML) based format designed to allow any CAD software to describe the shape and composition of any three-dimensional object to be fabricated on any additive manufacturing printer.

Further examples of design file formats include AutoCAD (.dwg) files, Blender (.blend) files, Parasolid (.x_t) files, 3D Manufacturing Format (0.3mf) files, Autodesk (3ds) files, Collada (.dae) files and Wavefront (.obj) files, although many other file formats exist.

Once obtained, a design file may be converted into a set of computer executable instructions that, once executed by a processer, cause the processor to control an additive manufacturing apparatus to produce a product according to the geometrical arrangement specified in the design file. The conversion may convert the design file into slices or layers that are to be formed sequentially by the additive manufacturing apparatus. The instructions (otherwise known as geometric code or "G-code") may be calibrated to the specific additive manufacturing apparatus and may specify the precise location and amount of material that is to be formed at each stage in the manufacturing process. As discussed above, the formation may be through deposition, through sintering, or through any other form of additive manufacturing method.

The code or instructions may be translated between different formats, converted into a set of data signals and transmitted, received as a set of data signals and converted to code, stored, etc., as necessary. The instructions may be an input to the additive manufacturing system and may come from a part designer, an intellectual property (IP) provider, a design company, the operator or owner of the additive manufacturing system, or from other sources. An additive manufacturing system may execute the instructions to fabricate the product using any of the technologies or methods disclosed herein.

Design files or computer executable instructions may be stored in a (transitory or non-transitory) computer readable storage medium (e.g., memory, storage system, etc.) storing code, or computer readable instructions, representative of the product to be produced. As noted, the code or computer readable instructions defining the product that can be used to physically generate the object, upon execution of the code or instructions by an additive manufacturing system. For example, the instructions may include a precisely defined 3D model of the product and can be generated from any of a large variety of well-known computer aided design (CAD) software systems such as AutoCAD®, TurboCAD®, DesignCAD 3D Max, etc. Alternatively, a model or prototype of the component may be scanned to determine the three-dimensional information of the component.

Accordingly, by controlling an additive manufacturing apparatus according to the computer executable instructions, the additive manufacturing apparatus can be instructed to print out one or more parts of the product. These can be printed either in assembled or unassembled form. For instance, different sections of the product may be printed separately (as a kit of unassembled parts) and then subsequently assembled. Alternatively, the different parts may be printed in assembled form.

In light of the above, embodiments include methods of manufacture via additive manufacturing. This includes the steps of obtaining a design file representing the product and instructing an additive manufacturing apparatus to manufacture the product in assembled or unassembled form according to the design file. The additive manufacturing apparatus may include a processor that is configured to automatically convert the design file into computer executable instructions for controlling the manufacture of the product. In these embodiments, the design file itself can automatically cause the production of the product once input into the additive manufacturing device. Accordingly, in this embodiment, the design file itself may be considered computer executable instructions that cause the additive manufacturing apparatus to manufacture the product. Alternatively, the design file may be converted into instructions by an external computing system, with the resulting computer executable instructions being provided to the additive manufacturing device.

Given the above, the design and manufacture of implementations of the subject matter and the operations described in this specification can be realized using digital electronic circuitry, or in computer software, firmware, or hardware, including the structures disclosed in this specification and their structural equivalents, or in combinations of one or more of them. For instance, hardware may include processors, microprocessors, electronic circuitry, electronic components, integrated circuits, etc. Implementations of the subject matter described in this specification can be realized using one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The method may comprise fitting the prosthesis. The method may comprise resecting the required amount of tibial and/or femoral bone to fit the prosthesis. The method may comprise using computer-guided surgery e.g. navigation systems or robotic systems.

The method may comprise implanting the prosthesis in a/the subject.

According to a second aspect of the invention, there is provided a design of a two-part joint prosthesis obtained or obtainable by the method according to the first aspect.

The features described in relation to the apparatus of the first aspect may equally apply in relation the design of the second aspect, and are not repeated here merely for reasons of brevity.

According to a third aspect of the invention, there is provided a two-part joint prosthesis obtained or obtainable by the method of the first aspect, or made based on the design according to the second aspect.

At least a portion of the two-part joint prosthesis may be 3D-printed. At least a portion of the two-part joint prosthesis may be 3D-bioprinted.

At least a portion of the prosthesis may be generated from cells, which may be allograft or autograft cells. Advantageously, the working surfaces of the prosthesis, e.g. of the knee prosthesis, may not be made of synthetic materials such as metal, polymers or ceramics, but may comprise, may consist essentially of, or may consist of cellular material. Thus, the implant or prosthesis may be designed to replicate the normal anatomy of the subject with two complementary components replicating the two bearing surfaces of the natural joint.

In an embodiment, the surfaces of bioprinted femoral, tibial and/or patellar components may comprise, may consist essentially of or may consist of hyaline cartilage and/or the supporting structures may comprise, may consist essentially of or may consist of subchondral bone and bone.

According to a fourth aspect of the invention, there is provided a computer program comprising computer executable instructions that, when executed by a processor, cause the processor to control an additive manufacturing apparatus to manufacture the prosthesis according to the third aspect.

For the avoidance of doubt, the features described in relation to any aspect may equally apply to any other aspect and are not repeated merely for reasons of brevity.

BRIEF DESCRIPTION OF DRAWINGS

Embodiments of the invention are described with reference to the accompanying drawings, in which.

DETAILED DESCRIPTION OF DRAWINGS

Figure 1:
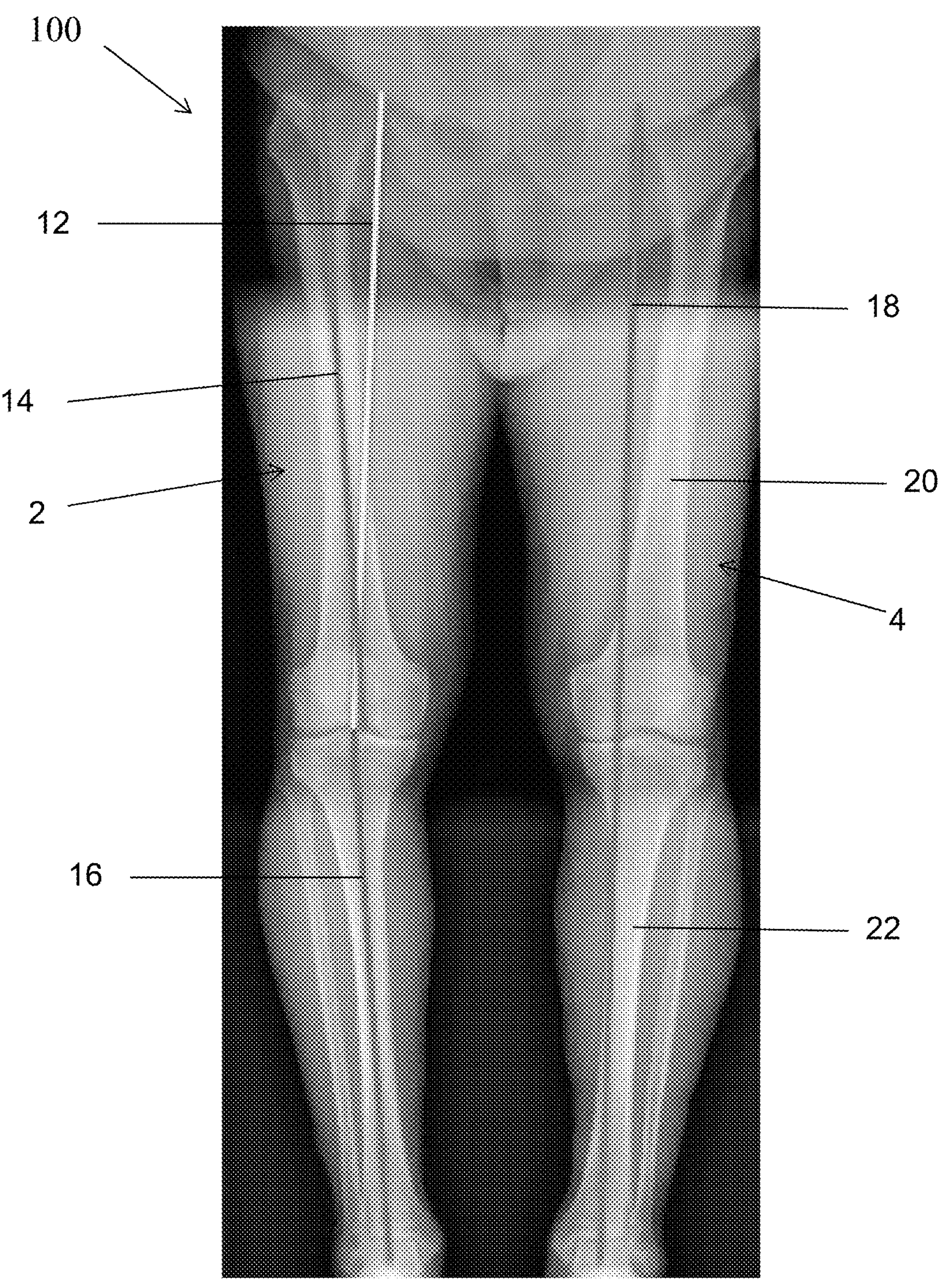
FIG. 1 shows a radiograph of a subject's legs showing alignments of lower limbs, femurs and tibias in the coronal plane.

FIG. 1 shows a radiograph 100 of a subject's legs showing alignments of legs, femurs and tibias in the coronal plane. On the right leg 2, line 12 represents the mechanical axis of the femur which refers to a line drawn from the centre of the femoral head to the centre of the knee. Line 14 represents the anatomical axis of the femur and refers to a line drawn along the centre of the intramedullary canal (broadly following the main axis of the diaphysis). The anatomical and mechanical axes of the tibia are both represented by line 16, and in FIG. 1 both coincide.

The global mechanical axis, also referred to as Maquet's line, labelled as line 18 on the left leg 4, extends from the femoral head to the centre of the talus. If this line 18 passes through the centre of the knee, it is considered that the knee is "balanced" or has no deformity in the coronal plane. In this example, line 18 passes through the medial (inner) side of the knee, which indicates a varus deformity.

In a conventional approach, in order to reduce the degree of varus alignment in the knee, a surgeon would use a conventional 3-part implant and adjust intra-operatively the dimensions, e.g. thickness, of the polyethylene implant in order to correct alignment. Alternatively, or additionally, intra-operative cut adjustments may be performed to the tibial and/or femoral bone(s) to which the implant is intended to be fixed.

In contrast, the method of the present invention comprises designing a two-part prosthesis, in this embodiment a knee implant. The method comprises determining and/or adjusting the dimensions, e.g. thickness, of at least one of the components of the implant design, in this embodiment of the tibial component or the femoral component, based on dynamic kinematic data of the subject's knee.

For simplicity, the embodiments described herein exemplify a procedure for designing a prosthesis for a unicompartmental knee arthroplasty (UKA), with the adjustment to correct a subject's knee deformity being applied to the tibial component or the femoral compartment. However, it will be understood that the teachings described herein may equally apply to a TKA procedure.

Unicompartmental knee arthroplasty (UKA) surgery may typically be carried out on patients with medial compartment osteoarthritis (OA). In these patients the medial compartment of the knee has worn away, leaving them with a varus deformity in their coronal alignment. The aim of the surgery is to replace the worn surfaces and to correct the coronal deformity to being close to neutral.

When a varus coronal deformity is corrected during surgery this typically causes a gap to appear in the medial compartment of the knee between the two bearing surfaces. This is illustrated in FIGS. 2 and 3.

Figure 2:
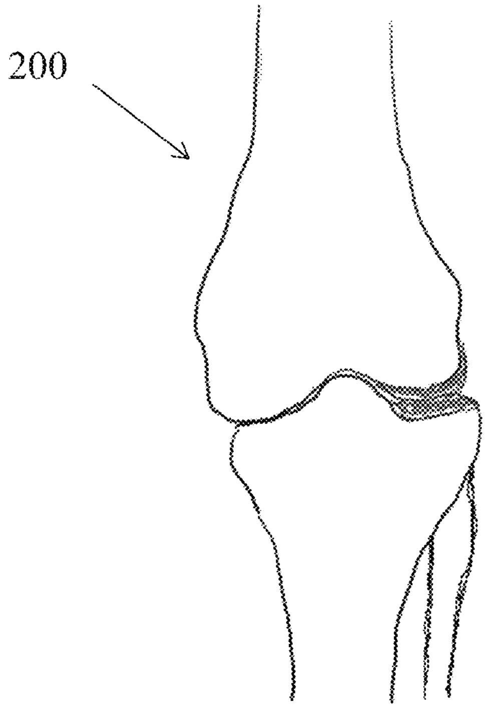
FIG. 2 shows and anterior-posterior (AP) view of a knee without valgus stress correction.
Figure 3:
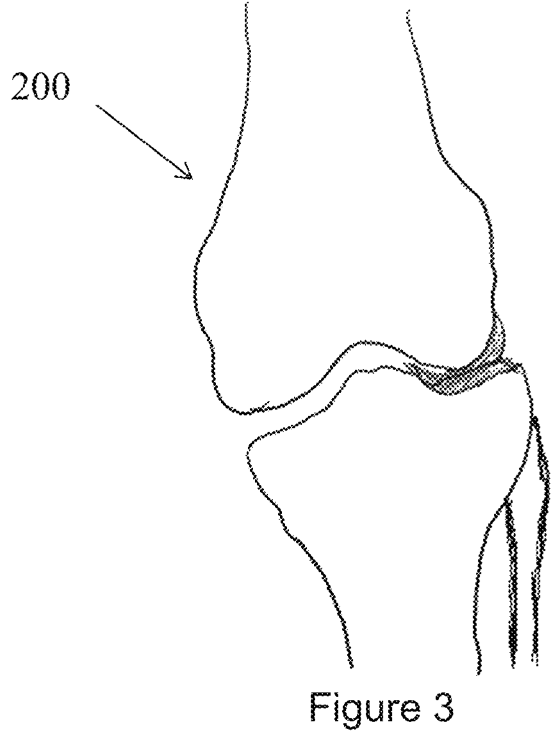
FIG. 3 shows an AP view of the knee of FIG. 2 with valgus stress correction using standardise force correction showing gap in medial compartment.

FIG. 2 shows and anterior-posterior (AP) view of knee 200 without valgus stress correction, and FIG. 3 shows an AP view of the knee with valgus stress correction using standardise force correction showing gap in medial compartment.

The size of the gap created depends of the angle of the deformity correction and can be calculated via trigonometry. This gap needs to be filled by the UKA implant. This is conventionally done by using different sizes of polyethylene inserts that sit between the tibial and femoral components, and is currently assessed and adjusted intra-operatively.

To create a two-component implant (femoral and tibial components), e.g. with a view to create a 3D bioprinted UKA, it is necessary to design a correctly sized 2-part implant for the patient pre-operatively. It is not possible to adjust the fit of the implant intra-operatively as per current practice. Therefore the size of the implant required to correct the coronal alignment deformity needs to be calculated pre-operatively.

When carrying out a UKA (unlike a TKA) the existing soft tissue envelope (ligaments around the knee) is maintained. It is therefore this soft tissue envelope that defines the correctability of the coronal alignment i.e. how close to neutral alignment the knee can go before the soft tissues constrain any further movement. This soft tissue envelope varies as the knee goes from extension to full flexion. Therefore the gaps created vary as the knee goes from extension to flexion. These gaps need to be calculated and this information used in the implant designs to ensure that the components are the correct thickness.

In an embodiment, the method comprises determining and/or adjusting the dimensions, advantageously the thickness, of the tibial component, based on dynamic kinematic data of the subject's knee.

Figure 4:
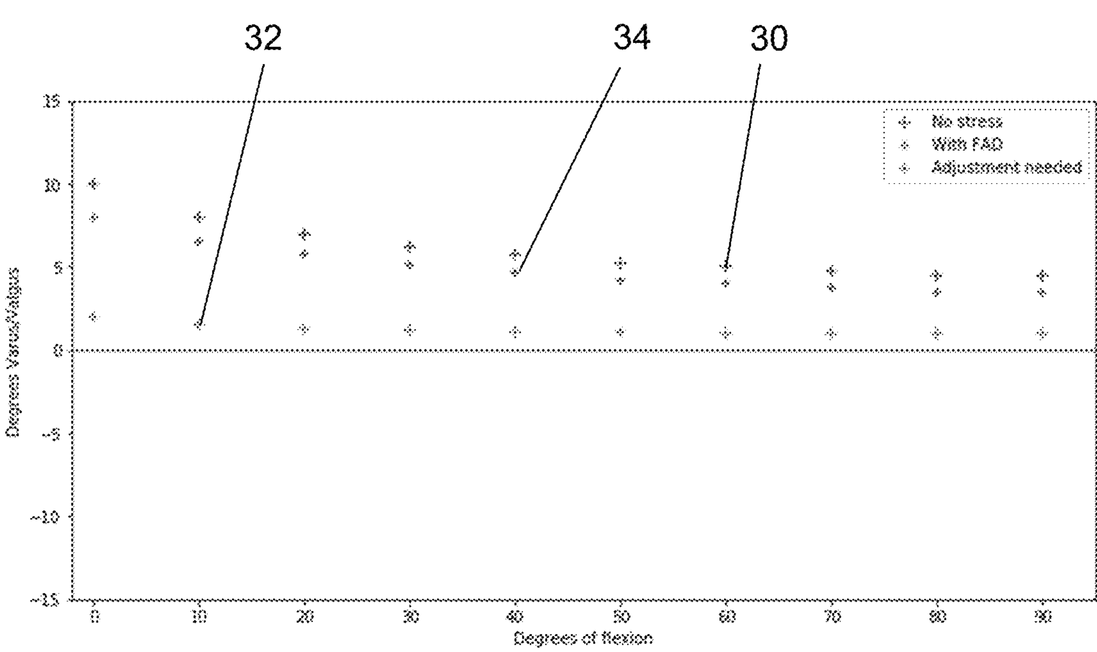
FIG. 4 shows a graph illustrating data processing of the alignment of a subject's joint according to an embodiment of the invention.

In the present embodiment, as illustrated in FIG. 4, we consider a varus knee with medial knee osteoarthritis, with 10° varus in full weight bearing.

In the present embodiment, the predetermined value to which the varus alignment should be corrected was selected as 2°.

Figure 5:
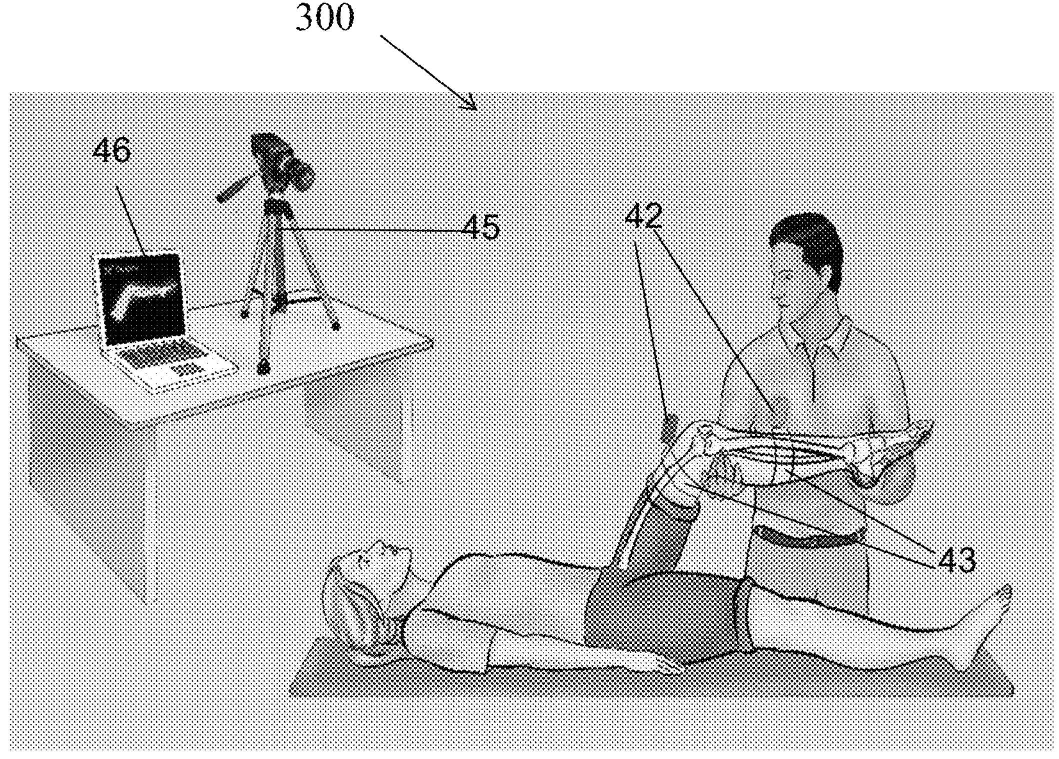
FIG. 5 shows an apparatus used for measuring the alignment angle in the coronal plane for various degrees of flexion of a subject's knee.

Alignment of the subject's knee in the coronal plane was measured in 10-degree increments between flexion angles of 0° and 90°. These measurements were carried out using a non-invasive measurement system 300, in this embodiment PhysioPilot®, as described in more detail below, and as shown in FIG. 5. The degree of varus alignment in the coronal place over the range of flexion is shown as "30" in FIG. 4.

Figure 6:
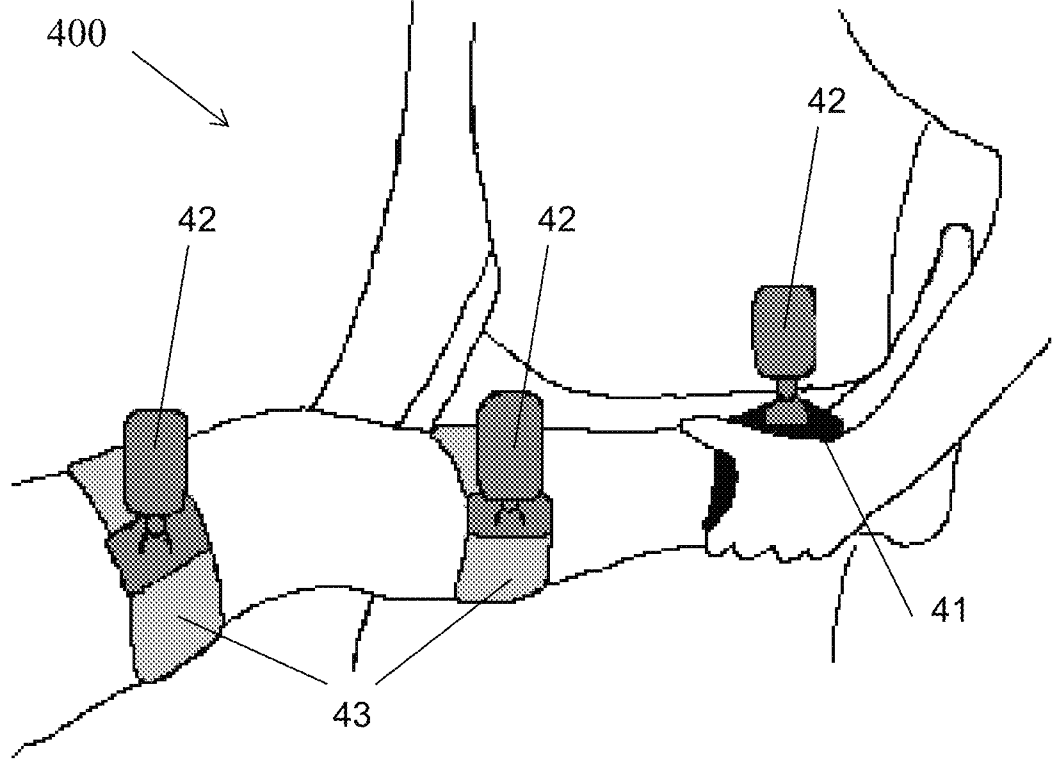
FIG. 6 shows an apparatus used for measuring the alignment angle in the coronal plane for various degrees of flexion of a subject's knee with application of any external force using a Force Measurement Device.

Alignment of the subject's knee in the coronal plane under full weight-bearing conditions was then measured under application of an external force on the subject's joint. The force was applied so as to reduce the varus alignment to the predetermined value of about 2°. These measurements were also carried out using a non-invasive measurement system 400, in this embodiment PhysioPilot®, as described in more detail below, and as shown in FIG. 6. The degree of varus alignment in the coronal place over the range of flexion is shown as "32" in FIG. 4. As shown in FIG. 6, a force measurement device 41 is held in the clinician's left hand and placed over the medial malleolus. The trackers 42 are attached to the lower limb with straps 43 and also another tracker is attached to the force measurement device 41. The clinician's right hand (unseen) is placed on the lateral epicondyle of the knee.

The difference between the alignment of the subject's knee in unloaded condition and under application of an external force, was then calculated, as shown as "34" in FIG. 4.

As mentioned above, in this embodiment, these measurements were also carried out using a non-invasive measurement system, in this embodiment PhysioPilot®.

In this system, as shown in FIG. 5 the subject is typically positioned supine with active infrared (IR) trackers 42 non-invasively secured to the distal thigh and proximal calf using straps and mounting plates 43. Movement is captured by a camera 45 connected to a computer 46. The subject is instructed to relax their leg muscles. Anatomical landmarks (femoral epicondyles, centre of the knee, ankle malleoli, anterior ankle centre) are palpated and kinematic hip and knee joint centres are located in three dimensions through a tracked sequence of clinical manoeuvres. These points are used to "register" the lower limb in order to determine coronal and sagittal mechanical femorotibial (MFT) angles. The coronal MFT angle (alignment) with the lower limb in maximum passive extension can then be recorded by supporting the limb only under the heel.

The passive range of motion of the knee, from full extension (0°) to full flexion (in this embodiment 90°), is then assessed. The knee is passively flexed with the clinician supporting the limb under the thigh and at the heel.

The anterior-posterior (AP) movement of the knee can also be measured using PhysioPilot® to confirm that the ACL is intact and that the patient is suitable for UKA. The AP laxity is measured using the Lachman test. The knee is held at 15°-30° of flexion as measured by the PhysioPilot®. The clinician holds the patient's thigh with one hand and the calf with the other with their thumb on the tibial tuberosity. The tibia (shank) is pulled forwarded and the amount of relative motion in mm to the femur (thigh) is recorded by PhysioPilot®. This measurement can be compared to known limits to determine whether the ACL is intact and so the patient is suitable for a UKA.

Knee laxity in the coronal plane can be quantified using varus and valgus stress manoeuvres applying manual force directly with one hand over the medial ankle malleolus and with the supporting hand placed over the lateral femoral epicondyle for a valgus stress or with one hand over the lateral ankle malleolus and with the supporting hand placed over the medial femoral epicondyle for varus stress. The application of the force is directed in the coronal plane and perpendicular to the mechanical axis of the tibia, as best illustrated in FIG. 6. During laxity assessment, the moment arm is determined as the perpendicular distance from the knee centre to the line of action of the applied force; this distance is determined by PhysioPilot® using the tracked force measuring device. When carrying out these varus and valgus stress manoeuvres the tracked force measuring device is used to measure the magnitude, point of application and direction of the force applied. This allows the actual moment being applied to the knee in the coronal plane to be calculated and so the laxity assessment can be standardised. During these stress manoeuvres, the knee is typically held at between 0° and 5° of flexion as indicated by the PhysioPilot® measurement of the sagittal MFT angle. If the knee cannot extend to 0° the stress measurements are performed within a 5° window of flexion from the maximum extension angle. The maximum possible angular correction of alignment in the coronal plane for a varus knee can be measured by applying a valgus stress to the knee as given above. This determines the corrected deformity that will be achieved intra-operatively. This measurement does not aim to reach a predetermined value but measures the limiting value of the soft tissue envelope i.e how much the knee malalignment can be corrected without altering the existing soft tissue envelope. This measurement of maximum possible correction can then be repeated at various levels of knee flexion through the range of motion with the PhysioPilot® measuring the knee flexion as well as the knee laxity. These measurements of corrected deformity will be specific to the individual being measured.

First Embodiment of Calculations: Single-Radius and Dual-Radius Designs

Having calculated the difference between the alignment of the subject's knee in full weight-bearing condition and under application of an external force, as shown in FIG. 4, an average of these values over the range of flexion was calculated. Advantageously, in this embodiment, the median average of the difference values was calculated. In the embodiment of FIG. 4, the median average adjustment was 4.4°.

Calculating the average, e.g., median average, allows a user to apply the calculated average as a target correction pre-operatively in the design of the knee prosthesis.

In this embodiment, two designs of the femur were used: single-radius and dual-radius.

Figure 16:
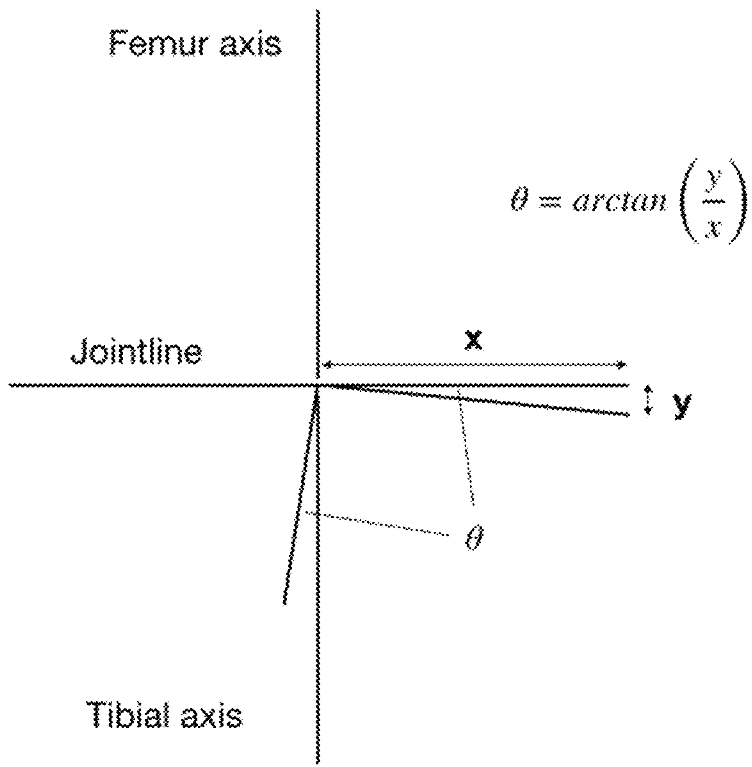
FIG. 16 shows a model used for calculating the size of the tibial component.

In the single radius design, the centre of rotation of the knee is known and the method involved calculating the size of the tibial component using model (1) as shown in FIG. 16, wherein θ is the adjustment angle, x is the distance from the joint axis to the distal part of the joint in mm, and y is the adjustment gap in mm.

The method then involved calculating the adjustment gap using equation (1):

$$y = x\tan(\theta) \qquad \text{Equation (1)}$$

Wherein θ is the adjustment angle, x is the distance from the joint axis to the distal part of the joint in mm, and y is the adjustment gap in mm.

Thus, knowing x, and having calculated θ, y can be calculated using equation (1).

Using the single-radius design, the adjustment gap will be a fixed number, and this design can be used to draw different varus/valgus curves over degrees of flexion for different y gap values.

Figure 17:
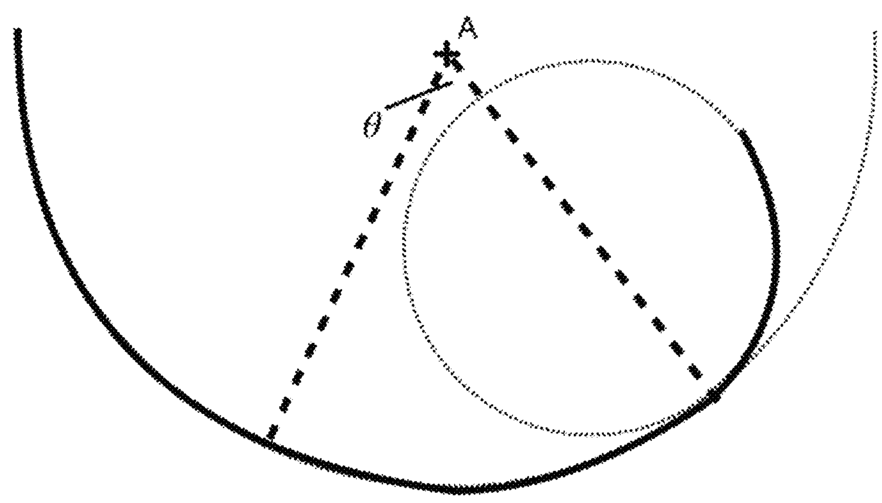
FIG. 17 shows a model used to represent a geometric construction of the femur in the sagittal view.

In the dual radius design, a geometric construction of the femur in the sagittal view can be represented by Model (2) as shown in FIG. 17.

The model is composed of two arcs from circles with different radii, with an internal tangential at a point during flexion. θ is the degree of flexion in the knee relative to the axis of rotation around point A from 0 to 90 degrees.

Figure 18:
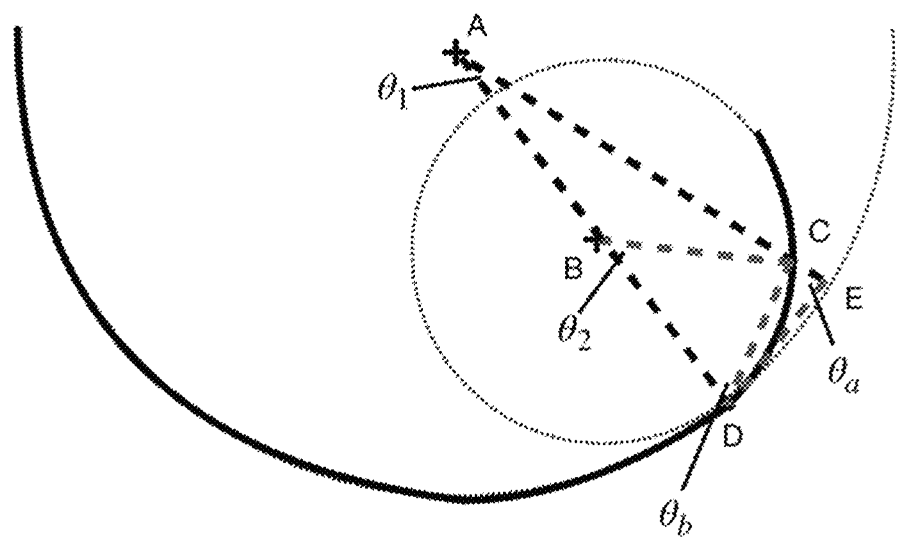
FIG. 18 shows a model used to represent a change in gap distance during rotation through in a dual-radius model.

To calculate the size of the tibial component in this case, the change in gap distance during the rotation through the dual-radius model is adjusted. This can be represented by Model (3) as shown in FIG. 18.

During rotation, the tibia reaches a point when the arc of the first circle and second circle are tangential (at point D). As the knee continues to rotate about point A (the centre of the knee), an adjustment in the calculate gap distance is needed as line CE brings the tibia closer to the centre of the knee than if the knee was modelled exclusively with an arc from the circle with the large radii. Thus, the method involves calculating CE is as a function of $\theta_1$ in order to calculate the loss in gap space over the range of motion (as the tibial will move up by distance CE once it reaches the tangent at point D.

In order to calculate CE, the method uses equation (2) (it will be appreciated that derivations may be performed for the different variables):

$$\Delta y^2 = X_1^2 + X_2^2 - 2X_1X_2\text{Cos}\left(\frac{-\theta_1 - \theta_2}{2}\right) \qquad \text{equation (2)}$$

Where CE=$\Delta y$;

CD=$X_1$

DE=$X_2$

From the equation (1), the gap value 'y' can be adjusted using the value for $\Delta y$ once the knee enters the angular range in the range of motion where the arcs are tangential such that $y=x\tan(\theta)-\Delta y$ (equation (3)).

Using this adjustment, we can perform the same calculations as above with the single radius model where we obtain a y-value where the median corresponds to the target correction value for θ. This calculated value 'y' corresponds to the required thickness of the tibial component in the two-part prosthesis.

Second Embodiment of Calculations

Figure 7:
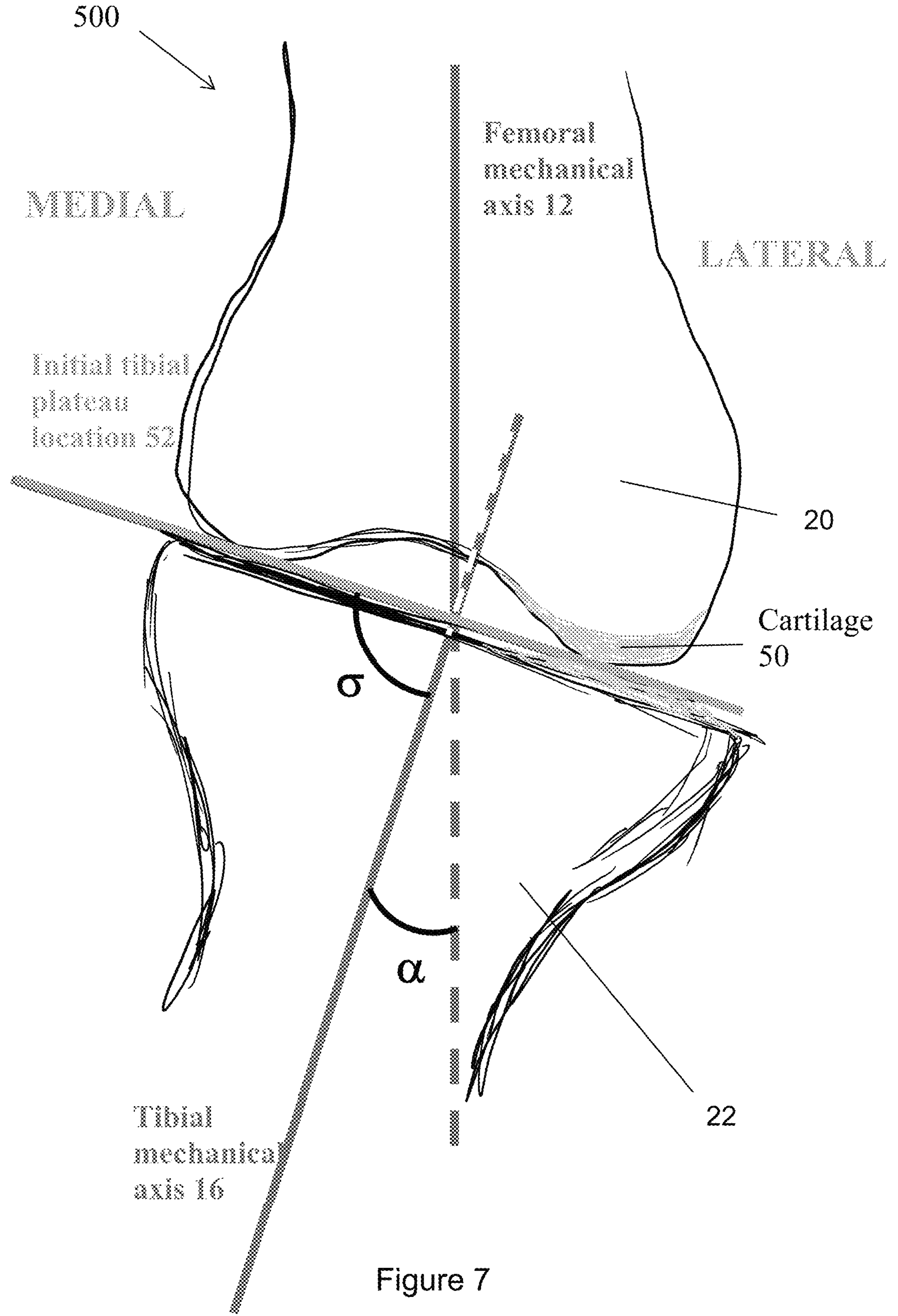
FIGS. 7-10 show schematic representations illustrating a method of designing a joint prosthesis according to an embodiment.
Figure 8:
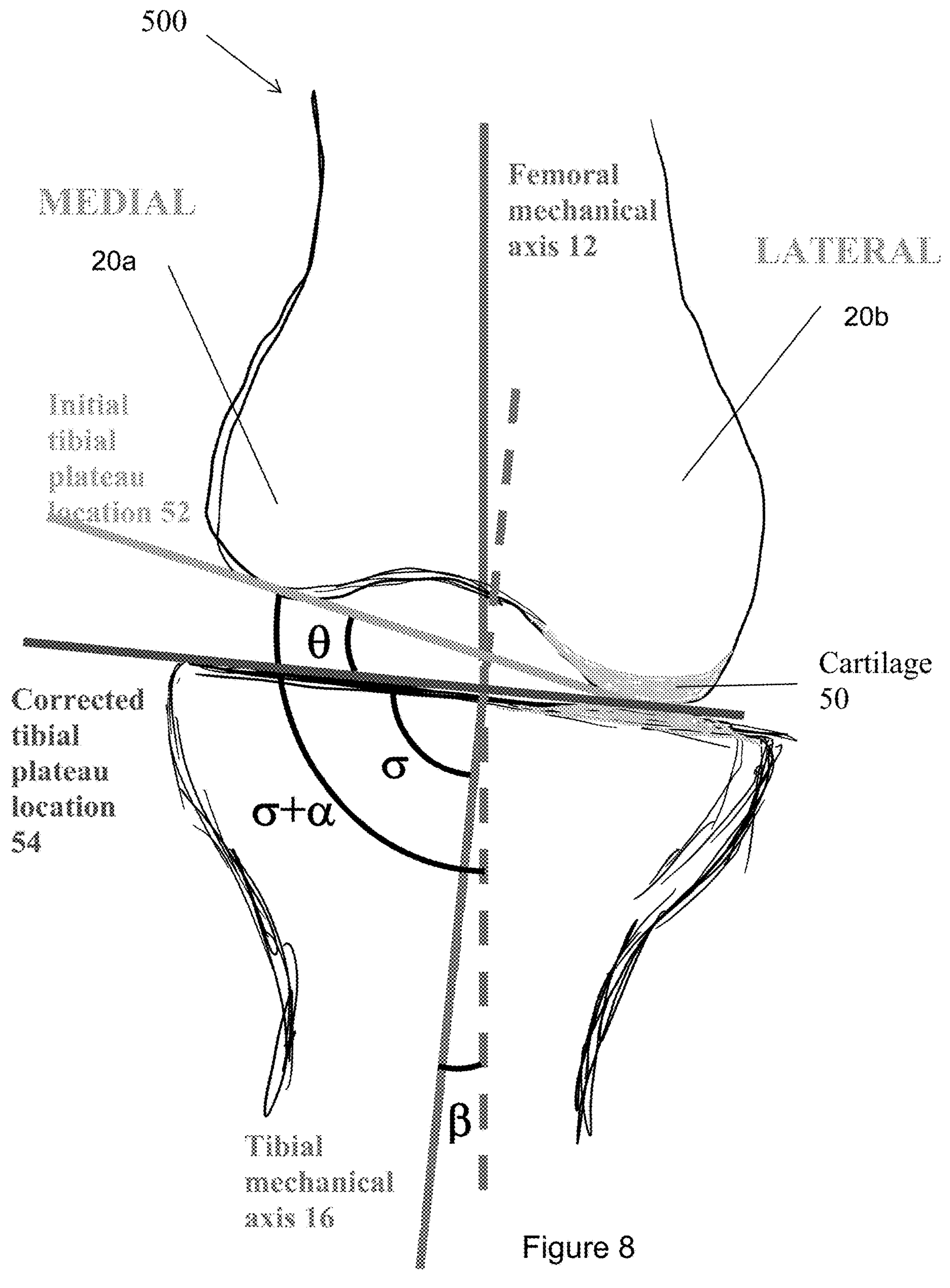
Figure 9:
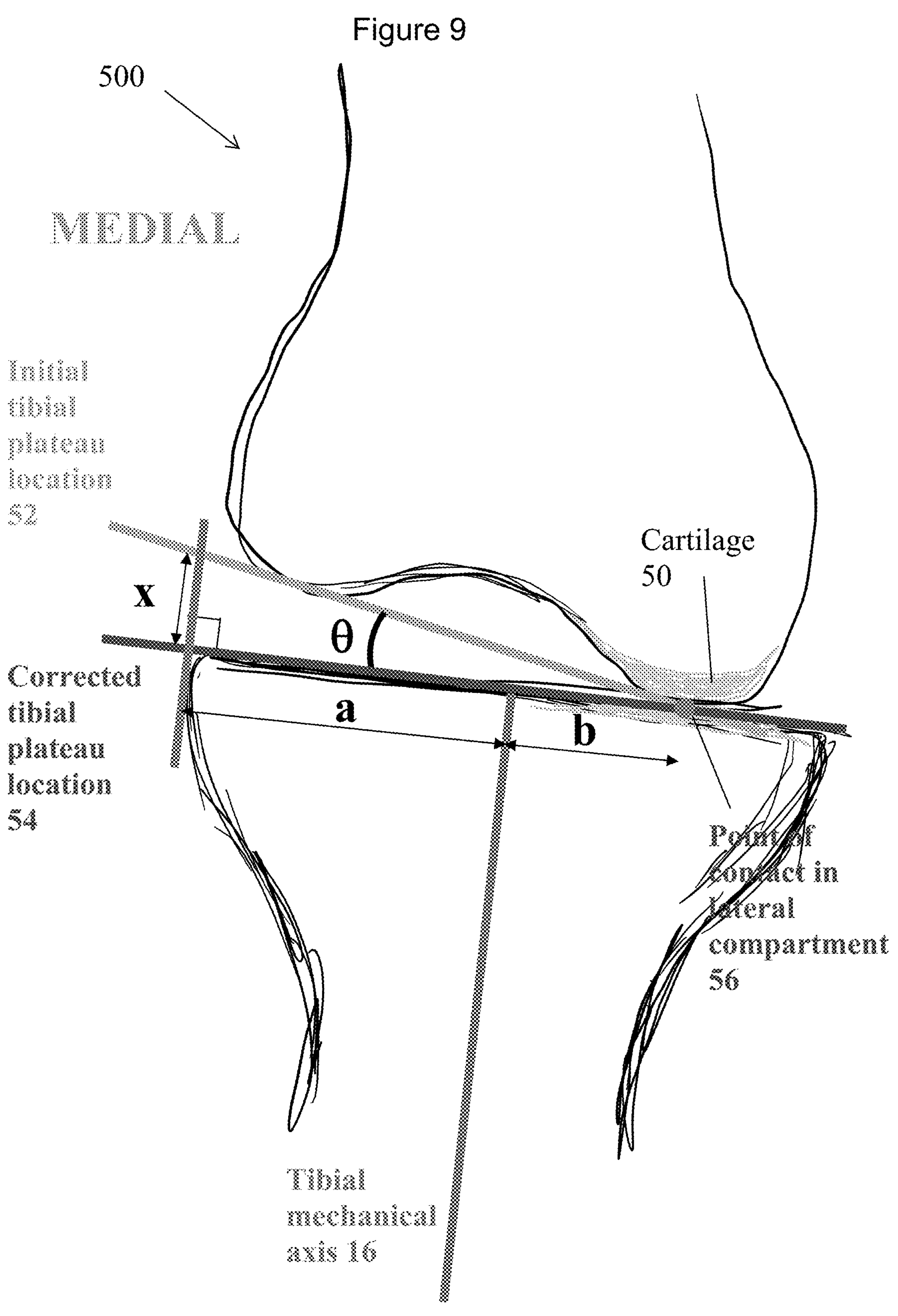

Based on the assumptions that the bearing surfaces of the medial compartment are in contact when the knee 500 is in its pre-operative (deformed) alignment (FIG. 7) and that when the alignment is corrected that the tibia pivots around the femur about the contact point in the lateral compartment (FIG. 8), if the width of the medial tibial plateau, the distance from the centre of the knee to the contact point in the lateral compartment and the correction angle are known the maximum gap that appears (at the medial edge of the tibia) can be calculated (FIG. 9). The required anatomical measurements can be taken from medical images such as X-ray, MRI, CT etc. The correction angle can be measured by PhysioPilot®. This correction angle is the maximum correction in coronal deformity as limited by the soft tissue envelope, with the corrected deformity being the limiting value of coronal alignment. FIGS. 7-9 show a knee having a femoral end 20 and a tibial end 22, and illustrate the femoral mechanical axis 12, the tibial mechanical axis 16, and the initial tibial plateau location 52.

In FIGS. 7-9:

| | |
|---|---|
| α | Initial deformity (no load) |
| β | Corrected deformity (applied load) |
| θ | Correction angle |
| σ | Angle between tibial mechanical axis 16 and tibial plateau 52 (tibial mechanical angle) |
| a | Width of medial tibial plateau (distance from knee centre to medial edge of the tibial plateau) |
| b | Distance from knee centre to point of contact 56 in the lateral compartment 20b |
| x | Maximum gap width due to deformity correction |

A trigonometrical calculation can be carried out at each knee flexion with the measured parameters above to calculate the maximum gap (x) throughout the range of motion. This assumes that the lateral compartment does not compress.

The correction angle is defined as $$\theta=\alpha-\beta \quad \text{(Equ 1)}$$

The angle between the initial tibial plateau location 52 and corrected tibial plateau location 54 (FIG. 8) is $$(\sigma+\alpha)-\alpha-\beta=\alpha-\beta=\theta \quad \text{(Equ 2)}$$

The maximum gap width (x) (FIG. 9) is $$x=(a+b)^*\tan\theta \quad \text{(Equ 3)}$$

Using Equation 3 the amount the prosthesis needs to be thickened to fill the gap (x mm) and give the correct coronal deformity correction at each degree of flexion through the range of motion can be calculated. For example:

a=40 mm b=20 mm

| Knee flexion (°) | Initial deformity | Corrected deformity | θ (°) | x (mm) |
|---|---|---|---|---|
| 0 | 10° varus | 2° varus | 8 | 8.4 |
| 10 | 10° varus | 2° varus | 8 | 8.4 |
| 20 | 10° varus | 2° varus | 8 | 8.4 |
| 30 | 9° varus | 1° varus | 8 | 8.4 |
| 40 | 9° varus | 1° varus | 8 | 8.4 |
| 50 | 9° varus | 1° varus | 8 | 8.4 |
| 60 | 9° varus | 2° varus | 7 | 7.4 |
| 70 | 8° varus | 2° varus | 6 | 6.3 |
| 80 | 8° varus | 2° varus | 6 | 6.3 |
| 90 | 8° varus | 3° varus | 5 | 5.2 |
| 100 | 7° varus | 3° varus | 4 | 4.2 |

A more complicated calculation can be carried out that assumes a small constant compression (z) of the lateral compartment 20*b* when a valgus load is applied. This is a better approximation of the true situation of the cartilage 50 being compressed under load. The maximum gap width with compression can be given as $x_z$.

Figure 10:
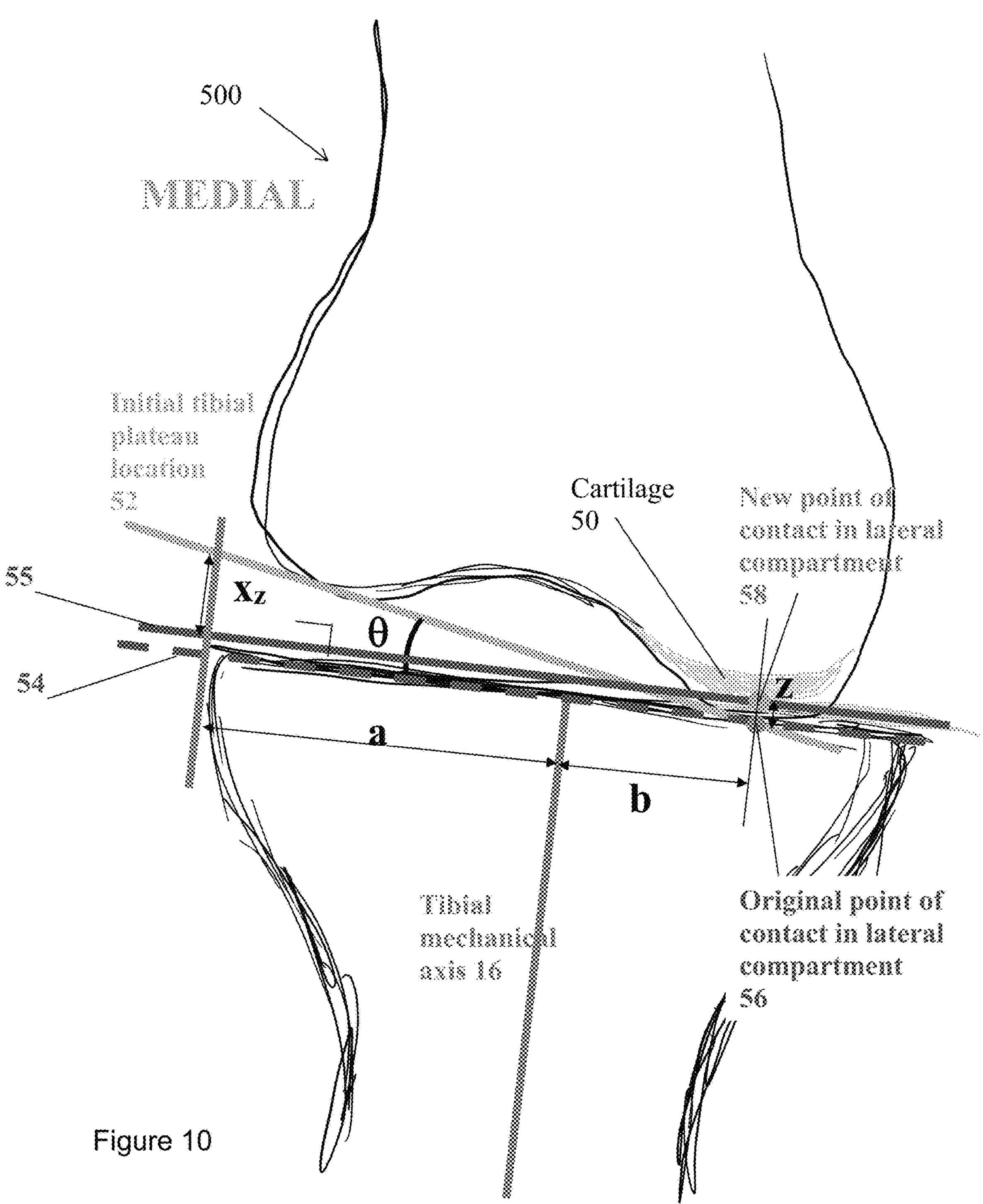

If the compression, z, is assumed to be in the direction parallel to tibial mechanical axis 16 (FIG. 10) then it can be seen that this would move the whole tibial plateau z mm in that direction moving the point of contact 58. It also changes the point where lines representing the original tibial plateau location 52 and corrected tibial plateau location 55 cross as this is no longer at the original point of contact 56. It can be seen that $x_z$ (x with compression) will be $$x_z=x-z \quad \text{(Equ 4)}$$

This adjustment can be applied to all the maximum gap widths calculated through the range of motion. A more complex model would also take into account that as the knee flexes that the point of contact 56 in the lateral compartment 20*b* moves around the tibial surface so that the distance b would also change as the point of contact 56 moved. This can be measured using a series of static medical images or modelled using published information on how the point of contact tracks during flexion [Kurosawa, H., P. S. Walker, S. Abe, A. Garg, and T. Hunter. "Geometry and motion of the knee for implant and orthotic design." Journal of biomechanics 18, no. 7 (1985): 487-499.].

An even more complex model can be created using the 3D imaging to create a solid model and then using Finite Element Analysis (FEA) techniques to model the knee. This could be generated with standard published material parameters for bone, cartilage and ligaments and then using the information gained from the kinematic assessment of the knee correction as boundary conditions and refining the material properties, particularly the ligaments, to make the model alignment for the applied load match that measured non-invasively. This model could then be used to directly measure the gaps through the range of motion. This model would include the compression of the cartilage 50 and the movement of the point of contact 56 without any specific assumptions.

The implant design can then be adjusted to ensure that these gaps are filled by the implant through the range of motion.

Using static and dynamic patient specific data, the above calculations allow a user to define the gap that needs to be filled to implement alignment correction. Adjustments of final implant position and orientation can be completed using both of these data. The thickness of both the tibia and the femur can then be implemented during manufacture of the prosthesis, e.g. of the tibial component in a UKA procedure, for example by 3D bioprinting the implant.

This can be repeated for a lateral UKA if necessary, mirroring the above methods.

An example is the implant is designed to fit a patient based on the medical imaging as per current practice. This uses the existing deformed anatomy to design a best fit implant. This would be sized to fit the current contact surfaces and the operation planned with specific bony resections to maintain the joint line. However these components would then need to be adjusted so that the deformity is corrected. This can be done by adding the calculated maximum gap widths to the thickness of the design.

Figure 11:
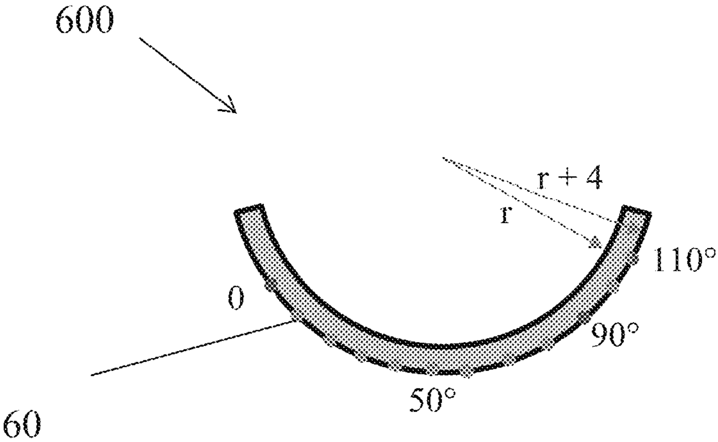
FIG. 11 illustrates a two-component UKA initial design for femoral component according to an embodiment.
Figure 12:
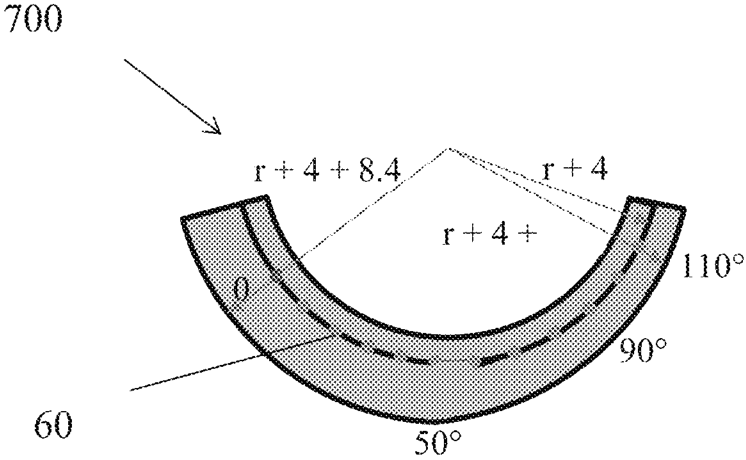
FIG. 12 illustrates a two-component UKA adjusted thickness design for femoral component according to an embodiment.

Example: In an embodiment, if a medial UKA implant 600 was designed based on a single radius femoral component with a thickness of 4 mm and a flat tibial component with a 3° posterior slope and thickness of 10 mm, in the sagittal plane a cross-section of the femoral component through the points of contact in the medial compartment 60 would be represented as per FIG. 11. This would be sized to be the best fit to the medical imaging data. The femoral component 700 design could then be adjusted based on the maximum gap calculations above, as shown in FIG. 12. The radii would be adjusted to ensure a smooth transition along the contact surface.

It can easily be seen that the adjustment does not depend on the initial design of the femoral component, whether it is a single, dual or multi-radius design the thickness will be adjusted in the same way. It can also be seen that the adjustment could be made partly on the femoral component and partly on the tibial component or all on the tibial component.

It will be clear to those skilled in the art that using this method it is possible to calculate the gap required to be filled for deformity correction at any point across the tibial plateau, not just at the medial or lateral edge, and then adjust the thickness of the implant to account for this.

Total Knee Arthroplasty (TKA)

Total knee arthroplasty (TKA) surgery is usually carried out on patients with both medial and lateral compartment OA. In these patients both compartments of the knee have worn away, often with one compartment wearing more than the other leaving them with a large deformity in their coronal alignment. They also often have a deformity in the sagittal plane, called a fixed flexion deformity. The aim of the surgery is to replace the worn surfaces and to correct the coronal and sagittal deformities to being close to neutral.

When carrying out a TKA (unlike a UKA) the soft tissue envelope (ligaments around the knee) is more often released intra-operatively to allow correction of coronal, sagittal and transverse alignment. There are also a number of different coronal alignment paradigms that can be employed by the surgeon: aiming for mechanical alignment (0° or 180° MFT angle); aiming for kinematic alignment (usually a few degrees of varus) or anatomical alignment (reproducing the average joint line coronal alignment i.e. 3° oblique joint line with 3° varus tibia and 3° valgus femur). The surgeon does not know the releases and adjustment to end up with good MFT alignment.

To be able to design a two-part TKA implant pre-operatively requires assumptions to be made. As per the UKA the knee kinematics can be measured non-invasively. This allows the assessment of any flexion contracture or hyper-extension and the assessment of any varus and valgus contracture. An example would be a knee with OA and an unloaded 20° varus coronal deformity and 15° fixed flexion contracture (FFC). The non-invasive assessment shows that the coronal alignment can be corrected to 8° varus and the sagittal alignment can be corrected to 10° FFC. If the surgeon wishes to go for kinematic alignment maintaining the soft tissue envelope that opening of the medial gap with 12° of correction can be calculated as above except that the point of rotation of the tibia around the femur will be the knee centre so b=0 in Equ 3 (due to both compartments having OA). This gap can then be added to thickness of the component(s) as described above.

However if the surgeon wishes to go for mechanical alignment there will be intra-operative releases of the soft tissues to get to around 1° varus and 0° FFC. In this case the opening of the medial gap with 190 of correction can be calculated as above except that the point of rotation of the tibia around the femur will be the knee centre so b=0 in Equ 3 (due to both compartments having OA). This gap can then be added to thickness of the component(s) as described above.

It should be clear that the methods listed here can be used with combinations of partial knee replacement implants i.e. combination of medial UKA, lateral UKA and patello-femoral joints are also possible [Heyse, Thomas Jan, Ahmed Khefacha, and Philippe Cartier. "UKA in combination with PFR at average 12-year follow-up." Archives of Orthopaedic and Trauma Surgery 130, no. 10 (2010): 1227-1230]. Further, different knee designs are possible such as TKA preserving only the posterior cruciate ligament (PCL) or both PCL and anterior cruciate ligament (ACL).

Figure 13:
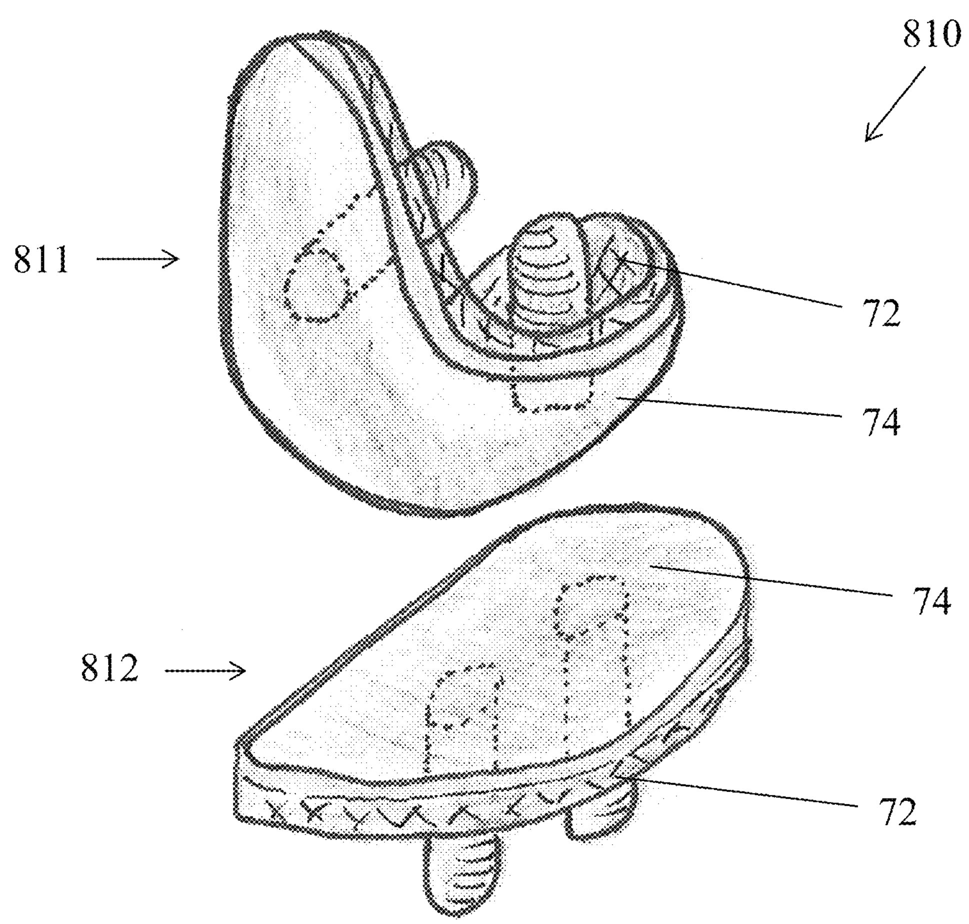
FIG. 13 illustrates a two-part knee prosthesis for a UKA, according to an embodiment of the present invention.
Figure 14:
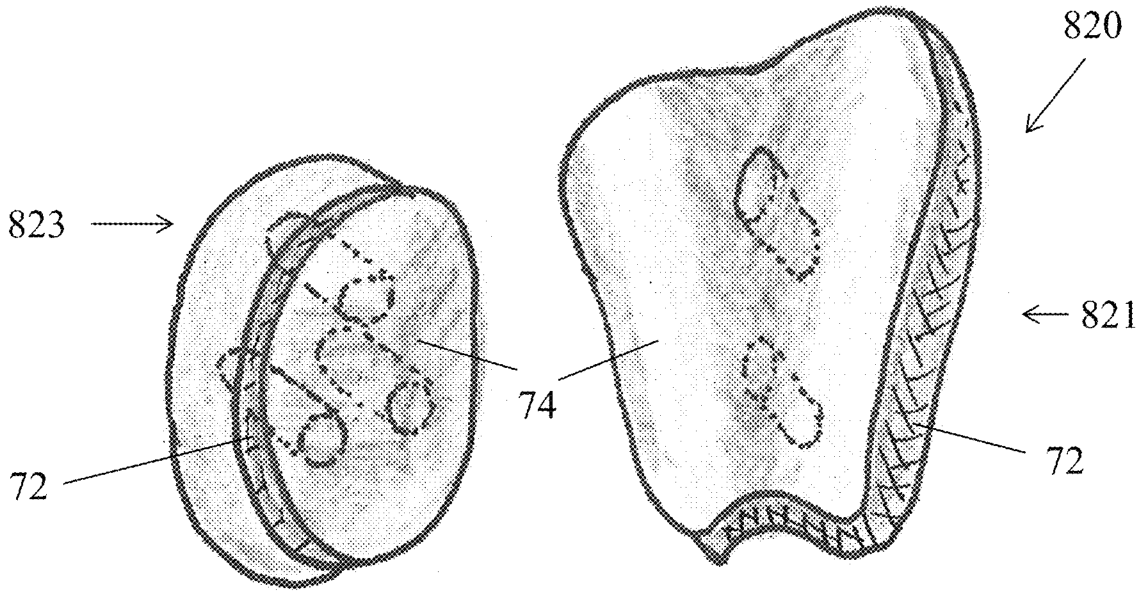
FIG. 14 illustrates a two-part knee prosthesis for a PFJR, according to an embodiment of the present invention.
Figure 15:
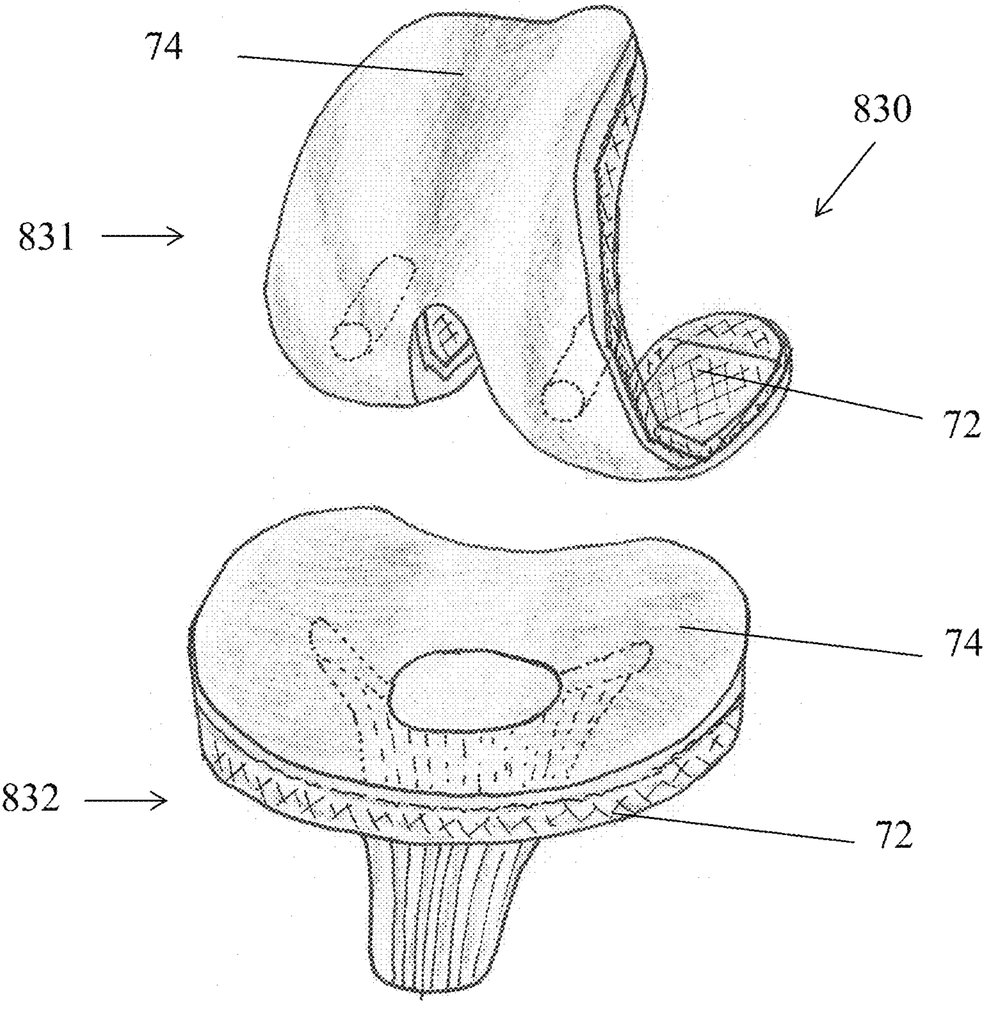
FIG. 15 illustrates a two-part knee prosthesis for a TKA, according to an embodiment of the present invention.

FIGS. 13-15 show two-part joint prostheses according to embodiments of the present invention.

FIGS. 13 and 14 illustrate two-part knee prostheses for partial knee replacement. FIG. 13 shows a prosthesis 810 for a UKA (unicompartmental knee arthroplasty), with femoral component 811 and tibial component 812. FIG. 14 shows a prosthesis 820 for a PFJR (patello femoral joint replacement), with femoral component 821 and patellar component 823.

FIG. 15 shows a two-part knee prosthesis 830 for a TKA (total knee arthroplasty), with femoral component 831 and tibial component 832.

As can be seen from FIGS. 13-15, each component of prostheses 810, 820 and 830 is made of subchondral bone and bone 72, and of cartilage 74. Thus, the prostheses 810, 820 and 830 do not include an insert, and allow for implantation of the prosthesis to correct a deformity in a subject's knee without the need for any intra-operative adjustments (typically done on the insert component).

Intraoperatively, a surgeon typically opens the knee in a conventional fashion and prepares the "implant bed" by resecting the exact amount of predetermined bone on the femur and the tibia, for example using computer guided surgery.

Once the preparation is complete, the surgeon typically performs the trial using a plastic model identical to the 3D bioimplant or other fixed sizes implant. The computer assisted measurements will confirm the plan and the surgeon will replace the plastic trial with the bioimplant starting with the tibia and then the femur. The soft tissue knee approach is then closed in a normal fashion.

It will be understood that the present embodiments are provided by way of example only, and that various modifications can be made to the present embodiments without departing from the scope of the invention.

The invention claimed is:

1. A method for designing a two-part knee prosthesis, the method comprising:

obtaining kinematic data of a subject's knee using non-invasive measurement of an alignment of the subject's knee in the coronal plane, comprising:

measuring the alignment of the subject's knee in the coronal plane without load at multiple degrees of flexion of the knee that are each between at least about 0° and about 45° of joint flexion; and measuring the alignment of the subject's knee in the coronal plane under application of an external force on the subject's knee so as to reduce or correct a varus or a valgus deformity, at each of the multiple degrees of flexion of the knee that are each between at least about 0° and about 45° of joint flexion;

calculating a difference between the alignment of the subject's knee without load at a respective degree of flexion of the multiple degrees of flexion of the knee and under application of the external force at the respective degree of flexion of the multiple degrees of flexion of the knee for each of the multiple degrees of flexion of the knee thereby obtaining a number of values for the difference;

calculating an average of the difference values; and designing the two-part knee prosthesis using the kinematic data by applying the average difference as a target correction in a pre-operative modelling and design of the subject's two-part knee prosthesis, wherein the two-part knee prosthesis comprises working surfaces and wherein the working surfaces of the two-part knee prosthesis comprise, consist essentially of or consist of cellular material.

2. A method according to claim 1, wherein the knee prosthesis comprises a femoral component and further comprises a tibial component or a patellar component.

3. A method according to claim 1, wherein the prosthesis is devoid of an insert.

4. A method according to claim 1, wherein at least a portion of the cellular material of the two-part knee prosthesis comprises three-dimensional (3D) bioprinted cells.

5. A method according to claim 4, wherein one or more cartilage portion(s), a subchondral bone portion, or a bone portion of the two-part knee prosthesis comprises the 3D bioprinted cells.

6. A method according to claim 4, further comprising determining a thickness of a femoral component and/or of a tibial component of the two-part knee prosthesis.

7. A method according to claim 6, further comprising determining the thickness of the femoral component and/or of the tibial component with respect to one or more parameters selected from the list consisting of cartilage thickness, thickness of sub-chondral bone, and cancellous bone thickness.

8. A method according to claim 1, further comprising adjusting a thickness of a femoral component and/or of a tibial component of a prosthesis design, based on the kinematic data of the subject's knee.

9. A method according to claim 1, further comprising measuring the alignment of the subject's knee in the coronal plane, with application of a weight-bearing load, between at least about 0° and about 45° of joint flexion.

10. A method according to claim 1, wherein the external force applied is selected so as to reduce or correct the varus or valgus deformity to a predetermined value or limiting value defined by a soft tissue envelope.

11. A method according to claim 1, wherein obtaining kinematic data comprises numerical quantification of a movement of the subject's knee in the coronal plane as an angle (°) and/or as a displacement (mm) value.

12. A method according to claim 1, wherein the average is a mean or a median of the difference values.

13. A method according to claim 1, comprising constructing the two-part joint prosthesis.

14. A method according to claim 1, comprising manufacturing the joint prosthesis using three-dimensional bioprinting.

15. A model of a two-part joint prosthesis obtained or obtainable by the method according to claim 1.

16. A two-part joint prosthesis obtained or obtainable by the method according to claim 1.

17. A two-part joint prosthesis according to claim 16, wherein at least a portion of the two-part joint prosthesis is three-dimensional bioprinted.

18. A computer program comprising computer executable instructions that, when executed by a processor, cause the processor to control an additive manufacturing apparatus to manufacture the prosthesis of claim 16.

* * * * *